United States Patent
Pettit et al.

(10) Patent No.: US 6,949,647 B2
(45) Date of Patent: Sep. 27, 2005

(54) SYNTHESIS OF PANCRATISTATIN

(75) Inventors: George R. Pettit, Paradise Valley, AZ (US); Noeleen Melody, Mesa, AZ (US)

(73) Assignee: Arizona Board of Regents, Tempe, AZ (US)

(*) Notice: Subject to any disclaimer, the term of this patent is extended or adjusted under 35 U.S.C. 154(b) by 0 days.

(21) Appl. No.: 10/450,917

(22) PCT Filed: Dec. 20, 2001

(86) PCT No.: PCT/US01/50652

§ 371 (c)(1),
(2), (4) Date: Jun. 17, 2003

(87) PCT Pub. No.: WO02/50023

PCT Pub. Date: Jun. 27, 2002

(65) Prior Publication Data

US 2004/0063675 A1 Apr. 1, 2004

Related U.S. Application Data

(60) Provisional application No. 60/257,785, filed on Dec. 21, 2000.

(51) Int. Cl.$^7$ .......................................... C07D 491/056
(52) U.S. Cl. .............................. 546/65; 546/61; 546/62
(58) Field of Search .............................. 546/65, 62, 61

(56) References Cited

U.S. PATENT DOCUMENTS 5,529,989 A   6/1996   Pettit et al.

OTHER PUBLICATIONS

Pettit, G.R. et al.: Synthesis of 10b–R–hydroxy–pancratistatin via narciclasine. J. Chem. Soc. Chem. Commun. pp. 2725–2726, 1994.*
Pettit, G.R. et al.: Antineoplastic agents.450.Synthesis of (+)–Pancratistatin from (+)–Narciclasine as relay. J. Org. Chem. vol. 66, pp. 2583–2587, 2001.*

* cited by examiner

*Primary Examiner*—Charanjit S. Aulakh
(74) *Attorney, Agent, or Firm*—Fennemore Craig, P.C.

(57) ABSTRACT

(+)-Narciclasine (2), available in quantity from certain *Amaryllidaceae* species or by total synthesis, is employed in for a ten step synthetic conversion (3.6% overall yield) to natural (+)-pancratistatin (1a). The key procedures involve the epoxidation of natural (+)-narciclasine (2) to an epoxide (6), reduction of the epoxide (6) to diol (8), formation of cyclic sulfate (12) and its ring opening with cesium benzoate followed by saponification of the benzoate to afford (+)-pancratistatin (1a).

2 Claims, 2 Drawing Sheets

Perspective crystal structure with atomic numbering of epoxide 6.

Crystal structure of diol acetate 8 (methanol solvent excluded).

SYNTHESIS OF PANCRATISTATIN

This application is the U.S. national stage of PCT/US01/50652 filed on Dec. 20, 2001, which claims the priority of U.S. Provisional Application Ser. No. 60/257,785 filed on Dec. 21, 2000, which is incorporated herein by reference.

This research was funded in part by Outstanding Investigator Grant CA44344-01-12 awarded by the Division of Cancer Treatment, National Cancer Institute, DHHS. The United States government may have certain rights to this invention.

INTRODUCTION

The present invention relates generally to the field of antineoplastic agents and more particularly to novel and unexpectedly beneficial methods of synthesizing pancratistatin, a known and highly effective anti neoplastic substance.

BACKGROUND OF THE INVENTION

Employing a 1980 Hawaii recollection of *Pancratium* (later reassigned *Hymenocallis*) *littorale* bulbs a very potent anticancer constituent was located. In 1984 the isolation (0.028% yield) and structure (by x-ray of the 7-meth-oxy derivative) of this important substance designated (+)-pancratistatin (1a). (See: Mohammad, R. M.; Limvarapuss, C.; Wall, N. R.; Hamdy, N.; Beck, F. W. J.; Pettit, G. R.; Al-Katib, A. *Int. J. Oncology* 1999, 15, 367–372). Subsequently, the U.S. National Cancer Institute initiated preclinical development of pancratistatin due to its high level of vitro and in vivo cancer cell growth inhibitory (including antiviral) (See: Gabrielsen, B.; Monath, T. P.; Huggins, J. W.; Kevauver, D. F.; Pettit, G. R.; Groszek, G.; Holingshead, M.; Kirsi, J. J.; Shannon, W. M.; Schubert, E. M.; DaRe, J.; Ugarkar, B.; Ussery, M. A.; Phelan, M. J. *J. Nat. Prod.* 1992, 55, 1569–1581; and (b) Gabrielsen, B.; Monath, T. P.; Huggins, J. W.; Kirsi, J. J.; Holingshead, M.; Shannon, W. M.; Pettit, G. R. In *Natural Products as Antiviral Agents*; Chu, C. K., Cutler, H. G., Eds.; Plenum: New York, 1992; pp 121–135) activity. Unfortunately, the preclinical development of this potentially important anticancer drug has been slowed by severe supply constraints and by its very low aqueous solubility (53 g/ml) properties. (See: Torres-Labaneira, J. J.; Davignon, P.; Pitha, J. *J. Pharm. Sci.* 1991, 80, 384–386). The latter problem was finally solved to a degree by the conversion of (+)-pancratistatin (1a) to a water soluble (>230 mg/ml) and comparably active phosphate (1b) prodrug (See: Pettit, G. R.; Freeman, S.; Simpson, M. J.; Thompson, M. A.; Boyd, M. R.; Williams, M. D.; Pettit, G. R. III; Doubek, D. L. *Anti-Cancer Drug Design* 1995, 10, 243–250). In addition, supplies of (+)-pancratistatin have been gradually increased by cloning and growing the plant in Arizona (See: Pettit, G. R.; Pettit, G. R. III; Groszek, G.; Backhaus, R. A.; Doubek, D. L.; Barr, R. J.; Meerow, A. W. *J. Nat. Prod.* 1995, 58, 756–759). However, a very efficient and commercially viable synthesis of this deceptively simple isocarbostyril is still needed and would be especially useful.

Considerable research efforts (See: Hoshino, O. *The Alkaloids*; Cordell, G. A. Ed.; Academic Press: vol. 51; San Diego, 1998; pp. 323) have been devoted to developing a practical synthesis of pancratistatin (1a). Four of these have led to pancratistatin. The first synthesis (See: Danishefsky, S.; Lee, J. Y. *J. Am. Chem. Soc.* 1989, 111, 4829–4837) provided racemic pancratistatin in 26 steps with an overall yield of 0.13%. The first enantioselective synthesis in 14 steps from bromobenzene (2% overall yield) of (+)-pancratistatin was reported by (See: Tian, X.; Hudlicky, T.; Königsberger, K. *J. Am. Chem. Soc.* 1995, 117, 3643–3644), in 1995. The same year, (See: Trost, B. M.; Pulley, S. R. *J. Am. Chem. Soc.* 1995, 117, 10143–10144) summarized a syntheses with an impressive 11% overall yield utilizing 13 steps. More recently, (See: Doyle, T. J.; Hendrix, M. M.; Van Der Veer, D.; Jaanmard, S.; Haseltine, J. *Tetrahedron* 1997, 53, 11153–11170) and (See: Magnus, P.; Sebhat, I. K. *Tetrahedron* 1998, 54, 15509–15524) (22 steps, 1.2% yield) have presented new synthesis of (+)-pancratistatin: In addition, a new synthesis of 7-deoxypancratistatin (1c) has been completed (13 steps, 21% overall yield) (See: Keck, G. E.; Wager, T. T-S; McHardy, S. F.; *J. Org. Chem.* 1998, 63, 9164–9165) and other new approaches to lactones 1a are in progress (See: Grubb, L. M.; Dowdy, A. L.; Blanchette, H. S.; Friestad, G. K.; Branchaud, B. P. *Tetrahedron Lett.* 1999, 40, 2691–2694; Aceña, J. L.; Arjona, O.; Iradier, F.; Plumet, J. *Tetrahedron Lett.* 1996, 37, 105–106; Gauthier, D. R.; Bender, S. L. *Tetrahedron Lett.* 1996, 37, 13–16).

From the beginning, the efforts to synthesize pancratistatin (1a) has focused on narciclasine (See: Ceriotti, G. *Nature* 1967, 213, 595–596; Okamoto, T.; Torii, Y.; Isogai, Y. *Chem. Pharm. Bull.* 1968, 24, 1119–1131; Mondon, A.; Krohn, K. *Chem. Ber.* 1975, 108, 445–463) (2) as the most attractive precursor, because it is available in practical quantities from the bulbs of certain *Amaryllidaceae* species. It has been studied in some detail (See: Rigby, J. H.; Mateo, M. E. *J. Am. Chem. Soc.* 1997, 119, 12655–12.656; Banwell, M. G.; Cowden, C. J.; Gable, R. W. *J. Chem. Soc. Perkin Trans.* 1 1994, 3515–3518; and Krohn, K; Mondon, A. *Chem. Ber.* 1976, 109, 855–876; Banwell, M. G.; Cowden, C. J.; Mackey, M. F. *J. Chem. Soc., Chem. Commun.* 1994, 61–62; Khaldi, M.; Chretien, F.; Chapleur, Y. *Tetrahedron Lett.* 1995, 36, 3003–3006; Park, T. K.; Danishefsky, S. J. *Tetrahedron Lett.* 1995, 36, 195–196; Angle, S. R.; Wada, T. *Tetrahedron Lett.* 1997, 38 7955–7958) leading to its recent synthesis in twelve steps by Hudlicky, starting from an enzymatic dihydroxylation of m-dibromo benzene (See: Gonzalez, D.; Martinot, T.; Hudlicky, T. *Tetrahedron Lett.* 1999, 40, 3077–3080). Earlier, the Cancer Research Institute at Arizona State University attempted to develop a practical synthesis of pancratistatin from narciclasine (2) and easily obtained 10b-R-hydroxy-pancratistatin (See: Pettit, G. R; Melody, N.; O'Sullivan, M.; Thompson, M.; Herald, D. L.; Coates, B. *J. Chem. Soc., Chem. Commun.* 1994, 2725–2726). But the last step, namely, the hydrogenolysis of the benzyl alcohol did not lead to (+)-pancratistatin. Through continuing effort, however, a successful synthesis of (+)-pancratistatin (1a) from (+)-narciclasine (2) in 3.6% overall yield has now been developed and that development forms the basis of this disclosure.

Attention is also directed to Dr. Pettit's earlier U.S. Pat. Nos. 4,866,071; 4,985,436; and 5,529,989 and particularly the background disclosed therein which is incorporated herein by this reference thereto.

BRIEF SUMMARY OF THE INVENTION (+)-Narciclasine (2), available in quantity from certain *Amaryllidaceae* species or by total synthesis, is employed as relay for a ten step synthetic conversion (3.6% overall yield) to natural (+)-pancratistatin (1a). The key procedures involve the epoxidation of natural (+)-narciclasine (2) to an epoxide (6), reduction of the epoxide (6) to diol (8), formation of cyclic sulfate (12) and its ring opening with cesium benzoate followed by saponification of the benzoate to afford (+)-pancratistatin (1a).

A principal object of the present invention is the development of an economically viable synthesis of pancratistatin using narciclasine as a relay.

These and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

As indicated above, the present invention relates generally to the field of chemotherapy and more particularly to an economically viable synthesis of the anti-neoplastic agent denominated "pancratistatin" which were discovered while, attempting to synthesize compounds related to certain *Amaryllidaceae*.

Statistical Definitions

The following measures are used to express drug activity giving the drug dose, which reduces cell growth to a specified percentage of growth:

$ED_{50}$ (P388) and $GI_{50}$ (HTCL) are the drug doses needed to reduce the percent growth to 50%. There is no mathematical difference between $ED_{50}$ and $GI_{50}$, which are both calculated using the same formula The only difference is historical usage.

TGI, (Total Growth Inhibition), is the drug dose needed to yield zero percent growth, e.g., just as many cells at the end of the experiment as were present in the beginning. Whether just as many cells were killed as were produced (steady state), or no growth occurred (total inhibition), cannot be distinguished.

$LC_{50}$, (Lethal Concentration 50%), is the drug concentration which reduces growth to −50%, i.e., removes half of the cells originally present at the beginning of the experiment.

Each drug is tested at five (5) doses: 100-10-1-0.1-0.01 µg/ml. Percent Growths are calculated for each dose. The two (or three) doses with growth values above, below, (or near to) 50% growth are used to calculate the $ED_{50}/GI_{50}$ using a linear regression formula. The log of the dose is used during the regression computation. If no dose yields a growth value under 50%, the results are expressed as: $ED_{50}$>(highest dose). If no dose yields a growth value higher than 50%, then $ED_{50}$<(lowest dose). Similar calculations are performed for the TGI at 0% growth, and at −50% growth for the $LC_{50}$.

Figure 1:
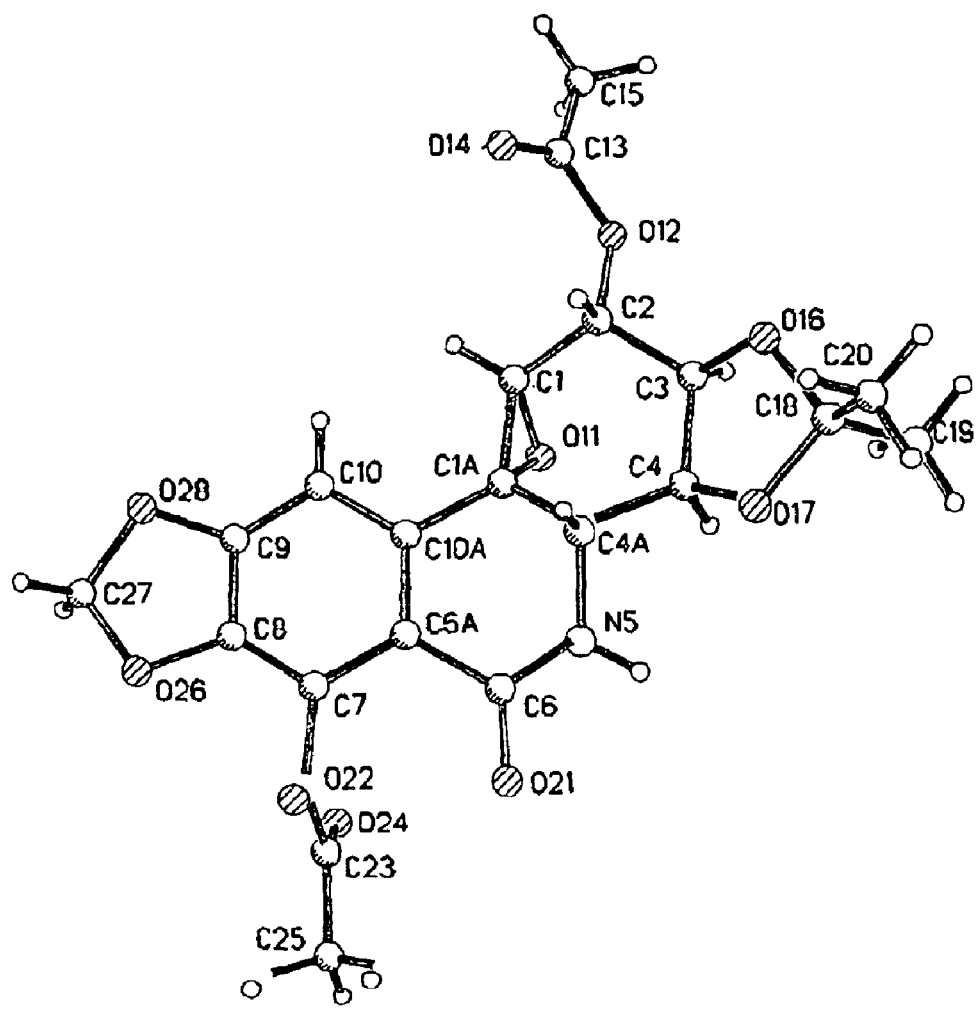
FIG. 1 is a perspective crystal structure with atomic numbers of epoxide 6.

The 3,4 acetonide of narciclasine (3) (See: Mondon, A.; Krohn, K. *Chem. Ber.* 1975, 108, 445–463) was prepared in 97% yield (See: Scheme 1 below) and the C-2 and C-7 hydroxyls were protected by acetylation to afford diacetate 4 in quantitative yield. However, an attempt at further purification using silica gel column chromatography caused some hydrolysis of diacetate 4 to monoacetate 5 in a ratio of 6:1 respectively. Oxidation of olefin 4 using m-chloroperoxybenzoic acid in dichloromethane and a phosphate buffer gave-epoxide 6 in 55% yield. The structure of epoxide 6 was confirmed by an x-ray structure determination using a crystal grown from acetone (FIG. 1). Hydrogenation of the epoxide in the presence of 10% palladium on carbon; followed by saponification gave a mixture (by 1H-NMR) of four compounds. These were separated by column chromatography on silica gel, isolated and identified by NMR. The methyl ether 7, trans B/C diol 8, cis B/C diol 9, and deprotected epoxide 10 were isolated in 19%, 28%, 27%, and 2% yields, respectively. Methylation of the C-1 hydroxyl group to provide ether 7 apparently occurred during the saponification step.

The overall yield of C-1-alcohol 8 from narciclasine was 15%. Detailed analysis of the NMR 2D COSY, 1H-1H correlation spectrum, allowed assignment of the hydrogen atoms. The NMR coupling constants (a 2.93, b 3.58, c 4.31, Jab=14.5 Hz, Jac=7.0 Hz) for alcohol 8 allowed assignment of the stereochemistry. These assignments were confirmed by an X-ray crystal structure determination using a crystal 8 grown from methanol solution (see FIG. 2).

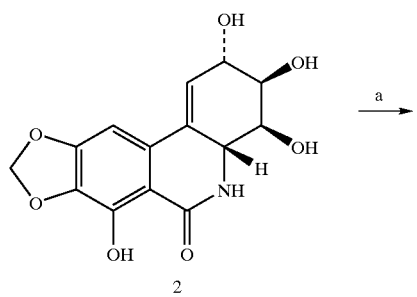

2

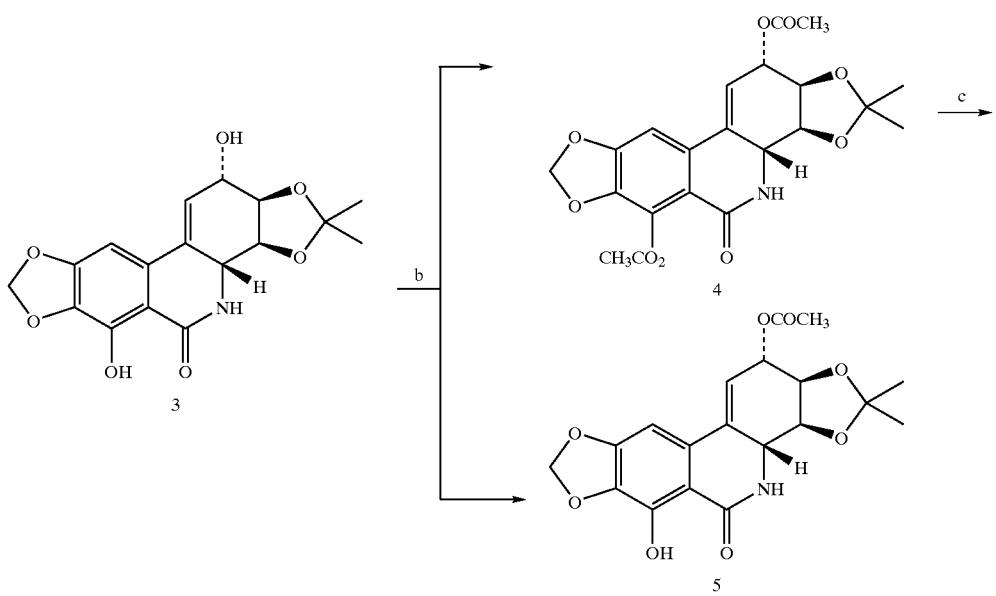
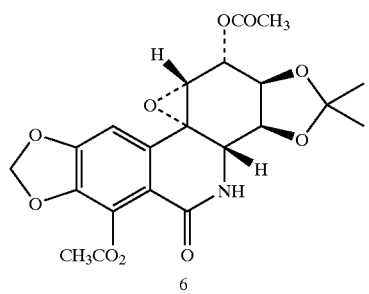
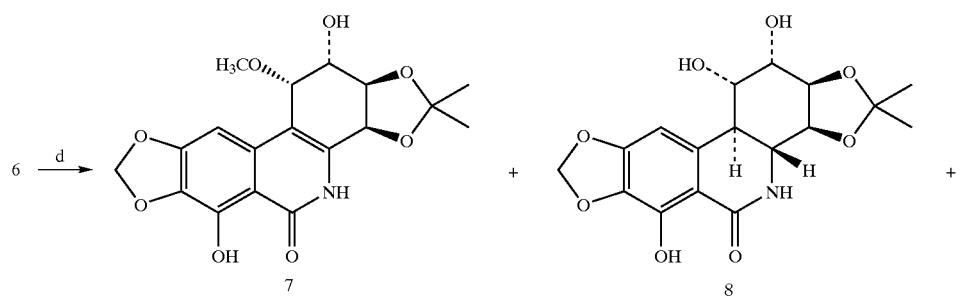
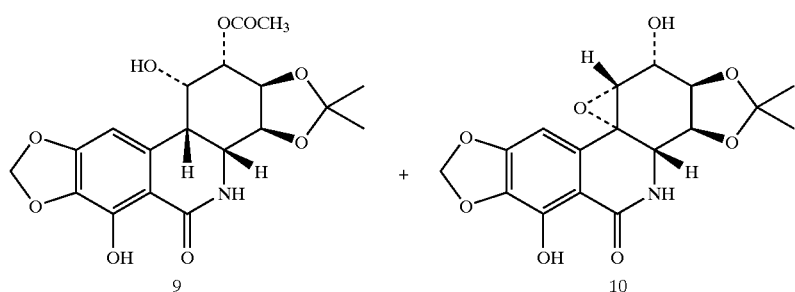

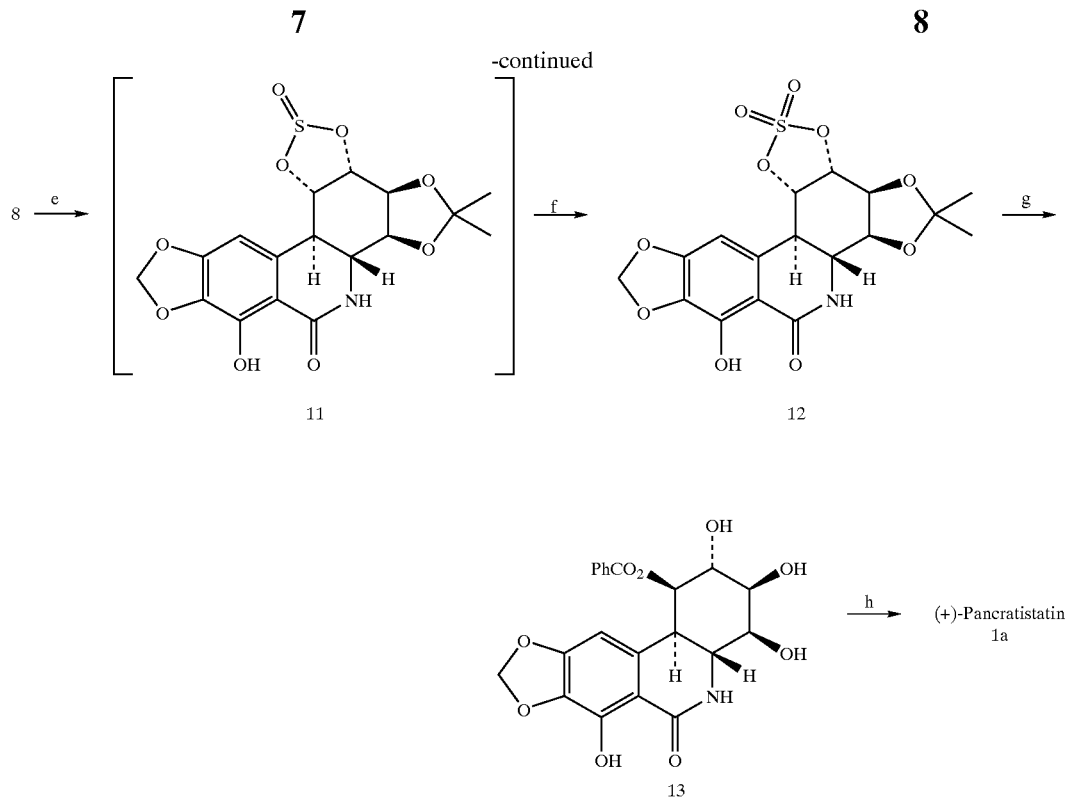

(a) DMF, DMP, PTSA;
(b) Ac₂O, pyr;
(c) m-CPBA, phosphate buffer;
(d) (i) H₂, 10% Pd/C; (ii) K₂CO₃, aq. CH₃OH:
(e) SOCl₂, Et₃N;
(f) RuCl₃. 3 H₂O/NaIO₄, CH₃CN, CCl₄, H₂O;
(g) (i) PhCO₂H, CS₂CO₃; (ii) THF/H₂O, cat. H₂SO₄;
(h) K₂CO2, CH₃OH.

Treatment of alcohol 8 with thionyl chloride led to a high yield of the corresponding epimeric (sulfoxide) cyclic sulfites 11. Oxidation (See: Trost, B. M.; Pulley, S. R. *J. Am. Chem. Soc.* 1995, 117, 10143–10144; Gao, Y.; Sharpless, K. B. *J. Am. Chem. Soc.* 1988, 110, 7538–7539; Kim, B. M.; Sharpless, K. B. *Tetrahedron Lett.* 1989, 30, 655–658; Jeong, L.; Marquez, V. *Tetrahedron Lett.* 1996, 2353–2356) of the cyclic sulfite epimers to the corresponding cyclic sulfate 12 was achieved using 0.5 equiv. of ruthenium trichloride with 3 equiv. of sodium iodate. Such reactions are usually performed using a catalytic amount of ruthenium trichloride and sodium iodate, but that procedure gave incomplete oxidation with only one of the epimeric sulfur atoms oxidized. Attempts to separate the mixture were not productive. However, using the excess oxidant method, cyclic sulfate 12 was obtained in 47% yield from alcohol 8.

Nucleophilic attack by cesium benzoate (See: Trost, B. M.; Pulley, S. R. *J. Am. Chem. Soc.* 1995, 117, 10143–10144; Gao, Y.; Sharpless, K. B. *J. Am. Chem. Soc.* 1988, 110, 7538–7539) on the cyclic sulfate 12 in dimethylforamide occurred over 4 hours. Hydrolysis of the alkyl sulfate in tetrahydrofuran using sulfuric acid allowed simultaneous cleavage of the acetonide to afford, following column chromatography, benzoate 13 in 74% yield. The benzoyl group was easily removed to give (+)-pancratistatin (1a) identical with the natural product (See: For the preceding contribution of this series, refer to Mohammad, R. M.; Limvarapuss, C.; Wall, N. R.; Hamdy, N.; Beck, F. W. J.; Pettit, G. R.; Al-Katib, A. *Int. J. Onicology* 1999, 15, 367–372. (b) Pettit, G. R.; Gaddamidi, V.; Cragg, G. M.; Herald, D. L.; Sagawa, Y. *J. Chem. Soc., Chem. Commun.* 1984, 1693–1694. (c) Pettit, G. R.; Gaddamidi, V.; Herald, D. L.; Singh, S. B.; Cragg, G. M.; Schmidt, J. M.; Boettner, F. E.; Williams, M.; Sagawa, Y. *J. Nat. Prod.* 1986, 49, 995–1002) (+)-Pancratistatin (1a) was obtained in 10 steps with an overall yield of 3.6% from narciclasine (2).

Synthetic conversion of (+)-narciclasine (2) to (+)-pancratistatin (1a) provided a useful opportunity to further study structure/activity relationships and the result (See: Table 1) was a clear demonstration that even minor structural modifications of pancratistatin (1a) led to decreased cancer cell growth inhibitory activity in all but the case of compound 13, where the activity was greatly enhanced by the presence of a C-1 benzoyl group.

TABLE I

Human Cancer and Murine Lymphocytic Leukemia Cell Line
Inhibition Values for Pancratistatin (1a) and Narciclasine (2) and Synthetic
Intermediates (3–13).

| | Cell Type | Cell line | 1a | 2 | 3 | 4 | 5 | 6 | 7 | 8 | 9 | 10 | 12 | 13 |
|---|---|---|---|---|---|---|---|---|---|---|---|---|---|---|
| $GI_{50}$ ($\mu g/ml$) | Pancreas-a | BXPC-3 | $2.8 \times 10^{-2}$ | $1.6 \times 10^{-2}$ | >10 | >10 | >10 | >10 | >10 | 8.8 | >10 | >10 | >10 | $9.4 \times 10^{-4}$ |
| | Ovarian | Ovcar-3 | $3.2 \times 10^{-2}$ | $1.6 \times 10^{-2}$ | >10 | >10 | >10 | >10 | >10 | 5.0 | >10 | >10 | >10 | $<1.0 \times 10^{-3}$ |
| | CNS | SF-295 | $1.7 \times 10^{-2}$ | $1.2 \times 10^{-2}$ | >10 | >10 | >10 | >10 | >10 | 7.2 | >10 | >10 | >10 | $1.3 \times 10^{-3}$ |
| | Lung-NSC | NCI-H460 | $4.8 \times 10^{-2}$ | $2.2 \times 10^{-2}$ | >10 | >10 | >10 | >10 | >10 | >10 | >10 | >10 | >10 | $<1.0 \times 10^{-3}$ |
| | Colon | KM20L2 | $2.6 \times 10^{-2}$ | $1.8 \times 10^{-2}$ | >10 | >10 | >10 | >10 | >10 | 6.9 | >10 | >10 | >10 | $<1.0 \times 10^{-3}$ |
| | Prostate | DU-145 | $1.6 \times 10^{-2}$ | $7.1 \times 10^{-3}$ | >10 | >10 | >10 | >10 | >10 | 3.8 | >10 | >10 | >10 | $<1.0 \times 10^{-3}$ |
| TGI ($\mu g/ml$) | Pancreas-a | BXPC-3 | $1.4 \times 10^{-1}$ | $4.5 \times 10^{-2}$ | >10 | >10 | >10 | >10 | >10 | >10 | >10 | >10 | >10 | $5.3 \times 10^{-3}$ |
| | Ovarian | Ovcar-3 | $1.1 \times 10^{-1}$ | $4.4 \times 10^{-2}$ | >10 | >10 | >10 | >10 | >10 | >10 | >10 | >10 | >10 | $1.9 \times 10^{-3}$ |
| | CNS | SF-295 | $9.1 \times 10^{-2}$ | $4.9 \times 10^{-2}$ | >10 | >10 | >10 | >10 | >10 | >10 | >10 | >10 | >10 | $4.9 \times 10^{-3}$ |
| | Lung-NSC | NCI-H460 | $4.3 \times 10^{-1}$ | $1.0 \times 10^{-1}$ | >10 | >10 | >10 | >10 | >10 | >10 | >10 | >10 | >10 | $1.1 \times 10^{-3}$ |
| | Colon | KM20L2 | $2.3 \times 10^{-1}$ | $1.2 \times 10^{-2}$ | >10 | >10 | >10 | >10 | >10 | >10 | >10 | >10 | >10 | $3.4 \times 10^{-3}$ |
| | Prostate | DU-145 | $10.0 \times 10^{-2}$ | $3.6 \times 10^{-2}$ | >10 | >10 | >10 | >10 | >10 | >10 | >10 | >10 | >10 | $2.6 \times 10^{-3}$ |
| $ED_{50}$ ($\mu g/ml$) | Murine Leukemia | P388 | 0.032 | 0.0044 | >10 | >10 | >10 | >10 | >10 | 2.6 | >10 | >10 | >10 | 0.0017 |

Experimental Section

Solvents were purified by redistillation. In addition, tetrahydrofuran was distilled from sodium benzophenone, dimethylformamide from phosphorous pentoxide and triethylamine from potassium hydroxide. Thin-layer chromatography was performed on MERCK KIESELGEL 60F254 plates eluting with the solvents indicated. Visualization was provided by a 254 mm UV lamp and development with a ceric sulfate spray/heat. Flash column chromatography was performed with MERCK silica gel 60 slurry packed in flash columns with the initiating solvent.

Melting points are uncorrected and were observed using a FISHER SCIENTIFIC hot stage melting point apparatus. Nuclear magnetic resonance spectra were acquired at either 300 MHz or 500 MHz for 1H and 75 MHz for 13C employing VARIAN-GEMINI 300 and INOVA 500 instruments. The EIMS were determined using a FINNIGAN-MAT Mass Spectrometer (Model 312) instrument. Analytical combustion analyses were performed by Galbraith Laboratories, Inc., Knoxville, Tenn. The X-ray data collection was performed with an ENRAF-NONIUS CAD4 diffractometer.

Narciclasine 3,4-acetonide (3) 10c

A solution prepared from natural (+)-narciclasine (2, 5g, 16.3 mmol), 2,2 dimethoxy-propane (25 ml) and p-toluene sulfonic acid (0.83 g) in DMF (25 ml) was stirred at room temperature for 16 hours. Pyridine (8.5 ml) followed by water (150 ml) was added to the suspension and the mixture stirred for 1 hour at room temperature. The precipitated product was collected, washed with water and dried (at 64° C. over $P_2O_5$ under high vacuum) to give narciclasine 3,4-acetonide (5.5 g, 97%) as an amorphous powder: m.p. 270–273° C., (lit. 10 c m.p. 275° C.), IR (Kbr) 3497, 3184, 1676, 1599, 1467, 1373, 1294, 1111, 1039 cm-1. $^1$HNMR (DMSO, 300 MHz) 13.7 (s, 1H); 8.8 (s, 1H); 7.01 (s, 1H); 6.47 (bs, 1H); 6.06 (m, 2H); 5.73 (bs, 1H); 4.2–3.9 (m, 4H); 1.45 (s, 3H); 1.31 (s, 1H) PPM. $^{13}$CNMR (DMSO, 300 MHz) 167.6, 152.5, 145.2, 133.3, 128.8, 128.3, 125.9, 109.8, 104.3, 102.0, 94.2, 79.0 PPM. EIMS m/z (%) 347 (M+, 28); 332 (1); 289 (2); 273 (6); 260 (8); 247 (100); 242 (22); 218 (10); 85 (2); 73 (10).

2,7-Di-acetoxy-narciclasine 3,4-acetonide (4) and 2-Acetoxy-narciclasine 3,4-acetonide (5)

Narciclasine 3,4-acetonide (3, 3.18 g, 9.15 mmol), was dissolved in acetic anhydride (20 ml)-pyridine (20 ml). The mixture was heated and stirred at 60° C. (under argon) for 24 hours. The suspension slowly dissolved. Ethyl acetate (300 ml) was added and the organic layer was washed with water (2×40 ml), dried ($Na_2SO_4$) and concentrated. The product was dried under high vacuum for 24 hours to remove traces of pyridine. The amorphous powder was examined by $^1$HNMR (CDCl$_3$) and found to be the diacetate (4) with a trace of pyridine still present. Column chromatographic purification was conducted on silica gel using a gradient elution system 1:99→1:9 ($CH_2Cl_2$—$CH_3OH$) to give the monoacetate (5), 0.15 g, 4.2%): r.f. 0.79 (98:2, $CH_2Cl_2$:$CH_3OH$), $[\alpha]^{27}_D$+84 (c 1.01, CHCl$_3$); m.p. 250–253° C.; $^1$H NMR (CDCl$_3$, 300 MHz) δ 12.85 (s, 1H); 6.65 (s, 1H); 6.4 (s, 1H). 6.09 (m, 2H); 5.36 (m, 1H); 4.3 (dd, J=5.4, 6.3 Hz, 1H); 4.12 (m, 2H); 2.18 (s, 3H); 1.51 (s, 3H); 1.37 (s, 3H); $^{13}$C NMR (CDCl$_3$ 300 MHz) 170.3, 167.6, 153, 146, 134.7, 128, 127.9, 121.5, 111.6, 104.9, 102.4, 94.5, 78.5, 75.3, 74, 55.2, 27.1, 24.9, 21.1; EIMS m/z (%): 389 (M+ 37); 331 (33); 289 (74); 271 (29); 260 (42); 247 (100); 242 (43); 218 (10); 85 (7); 44 (59). Anal. Calcd for $C_{19}H_{19}O_9N$: C, 58.6; H, 4.9; N, 3.59. Found: C, 58.2; H, 5.0; N, 3.4.

The diacetate (4, 3.2 g, 81%) exhibited: r.f. 0.6 (98:2: $CH_2Cl_2$: $CH_3OH$); $[\alpha]^{24}_D$=+60° (c 0.91, MeOH); m.p. 130–132° C.; $^1$H NMR (CDCl$_3$ 300 MHz) δ 6.97 (s, 1H); 6.12 (s, 1H); 6.08 (s, 2H); 6.01 (s, 1H); 5.37 (m, 1H); 4.40 (dd, J=5.7 Hz, 6.6 Hz, 1H); 4.12 (m, 2H); 2.38 (s, 3H); 2.21 (s, 3H); 1.51 (s, 3H); 1.38 (s, 3H); $^{13}$C NMR (CDCl$_3$ 300 MHz) 170.3, 169.2, 160.9, 152.4, 141.4, 134.0, 129.5, 128.5, 121.9, 113.4, 111.4, 103.0, 100.1, 78.7, 75.3, 73.8, 55.1, 27.11, 24.9, 21.1, 20.9; EIMS m/z (%) 431 M+, 14); 389 (60); 373 (28); 331 (75); 314 (9); 289 (100); 271 (35); 260 (42); 247 (99); 242 (39); 85 (9); 44 (95). Anal. Calcd for $C_{21}H_{21}O_9N \cdot CH_3OH$; C, 57.02; H, 5.43; N, 3.25. Found: C, 57.16; H, 4.99; N, 3.11.

1,10b-α-epoxy-2,7-diacetoxy-narciclasine 3,4-acetonide (6)

Diacetate 4 (3.0 g, 6.96 mmol) was dissolved in $CH_2Cl_2$ (180 ml) and phosphate buffer (pH8) (180 ml) was added followed by m-chloroperoxybenzoic acid (4.5 g, 26 mmol, 3.7 equiv.). The biphasic mixture was stirred for 16 hours whereby all the starting material had reacted (TLC). Dichloromethane (300 ml) was added and the organic layer separated and thoroughly washed with 5% $Na_2S_2O_3$ (3×300 ml), followed by 5% $Na_2CO_3$ (3×300 ml), water (3×300 ml), dried ($MgSO_4$) and concentrated. The crude product was washed with acetone and the white precipitate collected to give an amorphous solid (1.6 g, 52% yield). Recrystallization from hot acetone gave crystals which were examined (see below) by X-ray crystallography; m.p. 224–225° C.; $[\alpha]^{24}_D$=+138° (c 1.06, $CH_2Cl_2$); $^1H$ NMR (300 MHz $CDCl_3$) δ 6.46 (s, 1H); 6.1 (m, 2H); 5.86 (bs, 1H); 5.3 (d, J=6 Hz, 1H); 4.4 (dd, J=6.3, 6.9 Hz, 1H); 4.3 (t, J=8.7 Hz, 1H); 4.06 (s, 1H); 4.03 (d, J=8.4 Hz); 2.38 (s, 3H); 2.24 (s, 3H); 1.47 (s, 3H), 1.34 (s, 3H); $^{13}C$ NMR (300 MHz, $CDCl_3$) 170.5, 168.8, 161.3, 152.4, 142, 134, 128.4, 118.6, 109.38, 103.2, 101.1, 75.7, 75.4, 74.0, 58.1, 55.1, 53.4, 26.8, 24.2, 21.0, 20.8; EIMS M+(%); 447 (M+, 10); 405 (84); 345 (10); 287 (33); 258 (16); 234 (54); 44 (100). Anal. Calcd for $C_{21}H_{21}O_{10}N$. Calcd: C, 56.37; H, 4.73; N, 3.13. Found: C, 56.72; H, 4.83; N, 3.09.

X-Ray Crystal Structure Determination. Epoxide 6: A thick, plate-shaped X-ray sample (~0.70×0.60×0.40 mm) was obtained by crystallization from acetone. Data collection was performed at 293±1° K. Accurate cell dimensions were determined by least-squares fitting of 25 carefully centered reflections in the range of 35°<θ<40° using Cu K radiation.

Crystal Data: $C_{21}H_{21}O_{10}N_1$, FW=447.39, monoclinic, C2, a=18.200(4), b=9.2435(18), c=12.864(3), Å, β=105.73 (3)°, V=2083.2 (7) Å$^3$, Z=4, $ρ_c$=1.426 Mg/m$^3$, $μ$(CuKα)= 0.982 mm$^{-1}$,=1.54178 Å, F(000) 936.

All reflections corresponding to a complete quadrant (0<=h<=13, 0<=k<=9 , -19<=l<=19) were collected over the range of 0<2θ<110° using the ω/2θ scan technique. Friedel reflections were also collected (whenever possible) immediately after each reflection. Three intensity control reflections were also measured for every 60 minutes of X-ray exposure time and showed a maximum variation of 0.9% over the course of the collection. A total of 6050 reflections were collected. Subsequent statistical analysis of the complete reflection data set using the XPREP (The automatic space group determination program in the SHELXTL) program, verified that the space group as C2. After Lorentz and polarization corrections, merging of equivalent reflections and rejection of systematic absences, 2605 unique reflections (R(int)=0.0524) remained, of which 2583 were considered observed ($I_o$>2σ ($I_o$)) and were used in the subsequent structure determination and refinement. Linear and anisotropic decay corrections were applied to the intensity data as well as an empirical absorption correction (based on a series of psi-scans) (See: North, A. C.; Phillips, D. C.; Mathews, F. S. *Acta. Cryst.*, 1968 A2, 351). Structure determination was readily accomplished with the direct-methods program SHELXS (See: *SHELXFL-PC Version 5.101*, 1997, an integrated software system for the determination of crystal structures from diffraction data, Bruker Analytical X-Ray Systems, Inc., Madison, Wis. 53719. This package includes, among others: XPREP, an automatic space group determination program; XS, the Bruker SHELXS module for the solution of X-ray crystal structures from diffraction data; XL, the Bruker SHELXL module for structure refinement; XP, the Bruker interactive graphics display module for crystal structure). All non-hydrogen atom coordinates were located in a routine run using default values in that program. The remaining H atom coordinates for the parent molecules were calculated at optimum positions. All non-hydrogen atoms were refined anisotropically in a full-matrix least-squares refinement using SHELXL (See: *SHELXTL-PC Version 5.101*, 1997, an integrated software system for the determination of crystal structures from diffraction data, Bruker Analytical X-Ray Systems, Inc., Madison, Wis. 53719. This package includes, among others: XPREP, an automatic space group determination program; XS, the Bruker SHELXS module for the solution of X-ray crystal structures from diffraction data; XL, the Bruker SHELXL module for structure refinement; XP, the Bruker interactive graphics display module for crystal structure). The H atoms were included, their Uiso thermal parameters fixed at either 1.2 or 1.5 (depending upon their atomic environment) of the value of the Uiso of the atom to which they were attached and forced to ride that atom. The final standard residual $R_1$ value for 7 was 0.066 for observed data and 0.0663 for all data The corresponding Sheldrick R values were $wR_2$ of 0.1551 and 0.1555, respectively. The goodness-of-fit on $F^2$ was 1.101. The structure of epoxide 6 is shown in FIG. 1. The absolute stereochemistry of the epoxide (as shown), could be assigned with certainty based upon the value of the Flack absolute structure parameter, (See: Flack, H. D. *Acta Cryst.* 1983, 876881), i.e., -0.1(3). A final difference Fourier map showed minimal residual electron density; the largest difference peak and hole being +0.474 and -0.417 e/Å3. Final bond distances and angles were all within expected and acceptable limits.

1-Methoxy-Isonarciclasine 3,4-acetonide (7), 1-Isopancratistatin 3,4-acetonide (8), B/C Cis-1-Isopancratistatin 3,4-acetonide (9), 1,10b-α-epoxy-narciclasine 3,4-acetonide (10)

To a solution of epoxide 6 (1 g) in ethyl acetate (150 ml) was added 10% palladium-on-carbon (1 g). The flask was evacuated, flushed with hydrogen (×5) and hydrogenated at room temperature for 2.5 hours using a hydrogen-filled balloon. The palladium-on-carbon was removed by filtration and the filtrate was concentrated to dryness to give a white solid (0.94 g). The $^1H$ NMR ($CDCl_3$) indicated a mixture of products which was dissolved in 10% aq $CH_3OH$ (20 ml) and $CH_2Cl_2$ (10 ml). Potassium carbonate (0.6 g, 4.4 mol) was added and the mixture stirred overnight at room temperature. A precipitate slowly developed. The reaction mixture was neutralized using IR-120 H+ Amberlite resin. The resin was collected and the filtrate concentrated to a yellow solid (0.91 g). Additional epoxide 6, (3 g) was hydrogenated and the results of three such reactions were combined to give a yellow solid (2.65 g) which was purified by silica gel flash chromatography using 98:2 $CH_2Cl_2$—$CH_3OH$, to give 7 (0.46 g, 19%); 8 (0.68 g, 28%); a mixture of 9 and 10 (0.78 g); and 9 (0.31 g). The mixture of 9 and 10 was separated by dissolving in hot methanol and collecting the insoluble material (10, 0.051 g, 2%). Recrystallization of the mother liquor gave B/C cis-triol 9 (0.38 g). The total amount of the triol 9 recovered from the silica gel was 0.68 g, (27%). Recrystallization of diol 8 from hot methanol gave crystals which were used for X-ray crystal structure elucidation (see below). Methyl ether 7 corresponded to: r.f. 0.53 ($CH_2Cl_2$: $CH_3OH$, 4%); $[\alpha]^{24}_D$=15° (c 1.1, $CH_3OH$); m.p. 239–240° C.; $^1H$ NMR DMSO, 500 MHz) δ 12.8 (s, 1H); 9.39 (s, 1H); 6.77 (s, 1H); 6.1 (dd, J=3.5, 9.0 Hz, 2H), 5.17 (d, J=7.5 Hz, 1H), 4.68 (d, J=3 Hz, 1H), 4.63 (t, J=7 Hz, 1H); 3.86 (m, 1H); 3.42 (s, 3H); 258 (d, J=8 Hz, 1H); 1.48 (s, 3H); 1.46 (s, 3H); $^{13}C$ NMR (DMSO 500 MHz) 165.6, 154.4, 144.8, 134.3, 132.3, 111.5, 110.5, 108.5, 102.5, 92.9, 77.7, 74.8, 73.2, 71.5, 58.0, 27.2, 25.2. EIMS m/z (%): 377 (M+, 100), 362 (3), 349 (5), 319 (8), 288 (14), 270 (14), 258 (35), 247 (17), 292 (8), 218 (13), 101 (24), 56 (14), 44 (24), 28 (34). Anal. Calcd for $C_{18}H_{19}O_8N·CH_3OH$: C, 55.89; H, 5.39; N, 3.43. Found, C, 56.06; H, 5.39; N, 3.46.

Diol 8 was characterized with r.f. 0.39 (96:4 CH$_2$Cl$_2$:CH$_3$OH); [α]$^{24}_D$=−26° (c 0.48, CH$_3$OH); m.p. 231–232° C.; $^1$H NMR (CDCl$_3$ 500 MHz) δ 12.45 (s, 1H); 6.9 (s, 1H); 6.18 (s, 1H); 6.03 (narrow m, 1H), 4.38 (t, J=8 Hz, 1H); 4.31 (m, 2H); 3.92 (dd, J=5, 7.25 Hz, 1H); 3.57 (dd, J=14.5, 8.5 Hz, 1H); 3.05 (bs, 1H); 2.93 (dd, J-14.5, 7.5 Hz), 2.68 (bs, 1H); 1.48 (s, 3H), 1.38 (s, 3H); $^{13}$C NMR (CDCl$_3$, 500 MHz) 169.8, 153.2, 146.2, 135.4, 133.1, 110.9, 106.3, 102.3, 98.8, 77.6, 75.5, 70.8, 70.6, 52.9, 41.0, 27.3, 24.9. EIMS m/z (%): 365 (M+, 100), 350 (7), 290 (3), 272 (4), 260 (4), 234 (9), 205 (35), 190 (4), 176 (5), 147 (5), 85 (5), 73 (7), 60 (10), 44 (9), 28 (1). Anal Calcd for C$_{17}$H$_{19}$O$_8$N. Calcd: 55.89; H, 5.24; N, 3.83. Found: C, 55.5; H, 5.42; N, 3.85.

B/C-cis-diol 9 showed: R.f. 0.13 (96:4 CH$_2$Cl$_2$—CH$_3$OH) [α]$^{24}_D$=+27° (c 0.86, CH$_3$OH); m.p. 245° C.; $^1$H NMR (DMSO 500 MHz) δ 13.06 (s, 1H), 8.08 (s, 1H), 6.55 (s, 1H), 6.01 (s, 2H), 4.94 (d, J=6.5 Hz, 1H), 4.53 (d, J=4 Hz, 1H), 4.38 (d, J=4.5 Hz, 1H), 4.1 (d, J=5.5 Hz, 1H), 4.05 (dd, J=8.5, 5.5 Hz, 1H), 3.58 (m, 1H), 3.52 (m, 1H), 3.01 (m, 1H), 1.42 (s, 3H), 1.29 (s, 3H); $^{13}$C NMR (DMSO 500 MHz) 169.5, 151.5, 144.4, 135.7, 131.9, 108.6, 107.1, 101.6, 99.5, 76.1, 75.5, 74.9, 71.9, 49.6, 38.7, 28.3, 26.5. EIMS mz (%): 365 (M+, 100); 350 (6), 305 (3.5), 258 (7), 234 (31.6), 205 (77), 176 (7), 176 (7), 147 (10), 119 (5), 100 (9), 85 (12), 73 (17.5), 60 (24), 44 (22), 28 (22). Anal. Calcd: C$_{17}$H$_{19}$O$_8$N.H$_2$O Calcd: C, 53.3; H, 5.5; N, 3.6. Found C, 53.6; H, 5.5; N, 3.6.

Epoxide 10: R.f. 0.15 (96:4 CH$_2$Cl$_2$—CH$_3$OH); [α]$^{22}_D$=−4.2° (c 0.57, THF); m.p. 242–244° C.; $^1$H NMR (DMSO 300 MHz) δ 11.9 (s, 1H), 6.83 (s, 1H), 6.12 (s, 1H), 5.09 (dd, J=9, 11 Hz, 1H), 4.96 (d, J=10 Hz, 1H), 4.66 (dd, J=3.6, 6 Hz, 1H), 4.33 (dd, J=6.6, 3 Hz, 1H), 3.53 (m, 1H), 1.38 (s, 3H), 1.36 (s, 3H); $^{13}$C NMR (DMSO, 300 MHz) 166.4, 154.2, 144.3, 132.0, 131.3, 114.9, 109.9, 108.9, 102.9, 100.2, 94.5, 76.2, 72.4, 71.2, 66.3, 28.7, 26.7. EIMS m/z (%): 363 (M+, 100), 345 (5), 305 (22), 288 (10), 276 (13), 258 (39), 233 (21), 205 (11), 60 (14), 44 (33), 28 (34).

X-Ray Crystal Structure Determination. Diol acetonide 8: A plate-shaped crystal (~0.35×0.20×0.10 mm) was obtained by crystallization from methanol and mounted in a sealed capillary with the specimen immersed in mother liquor. Data collection was performed at 293±1° K. Accurate cell dimensions were determined by least-squares fitting of 25 carefully centered reflection in the range of 35°<θ<40° using Cu Kα radiation.

Crystal Data: C$_{17}$H$_{19}$O$_8$N$_1$ 1 CH$_3$OH, FW=397.37, triclinic, P1, a=7.9890(12), b=9.072(2), c=13.564(2) Å, α=87.805(16), β=82.317(13), =Y71.734(16)°, V=925.1(3) Å$^3$, Z=2, ρ$_c$=1.426 Mg/m$^3$, μ (CuKα)=0.982 mm$^{-1}$, =1.54178 Å, F(000) 420.

Figure 2:
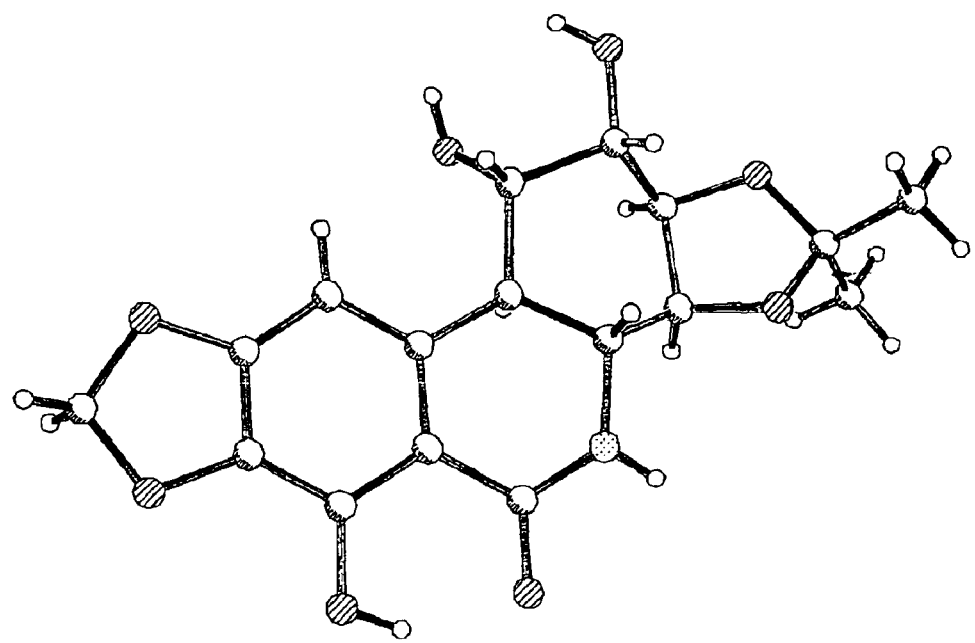
FIG. 2 is a crystal structure of diol acetonide 8 (methanol solvent excluded).

All reflections corresponding to a complete hemisphere (0<=h<=9, −10<=k<=10, −15<=l<=15) were collected over the range of 0<2θ<120° using the ω/2 scan technique. Friedel reflections were also collected (whenever possible) immediately after each reflection. Three intensity control reflections were also measured for every 60 minutes of X-ray exposure time and showed a maximum variation of −1.5% over the course of the collection. A total of 6235 reflections were collected. Subsequent statistical analysis of the complete reflection data set using the XPREP (See: The automatic space group determination program in the SHELXTL) program, verified that the space group as P1. After Lorentz and polarization corrections, merging of equivalent reflections and rejection of systematic reflections, a total of 5550 were considered observed (I$_o$>2σ(I$_o$)) and were used in the subsequent structure determination and refinement. Linear and anisotropic decay corrections were applied to the intensity data as well as an empirical absorption correction (based on a series of psi-scans) (See: North, A. C.; Phillips, D. C.; Mathews, F. S. Acta. Cryst., 1968 A2, 351). The structure was solved with the direct-methods program SHELXS (See: SHELXTL-PC Version 5.101, 1997, an integrated software system for the determination of crystal structures from diffraction data, Bruker Analytical X-Ray Systems, Inc., Madison, Wis. 53719. This package includes, among others: XPREP, an automatic space group determination program; XS, the Bruker SHELXS module for the solution of X-ray crystal structures from diffraction data; XL, the Bruker SHELXL module for structure refinement; XP, the Bruker interactive graphics display module for crystal structure). All non-hydrogen atom coordinates were located in a routine run using default values in that program. The asymmetric unit (i.e., unit cell) was found to contain two independent molecules of the parent compound, as well as two molecules of disordered methanol solvent. The remaining H atom coordinates for the parent molecules were calculated at optimum positions. All non-hydrogen atoms were refined anisotropically in a full-matrix least-squares refinement using SHELXL (See: SHELXTL-PC Version 5.101, 1997, an integrated software system for the determination of crystal structures from diffraction data, Bruker Analytical X-Ray Systems, Inc., Madison, Wis. 53719. This package includes, among others: XPREP, an automatic space group determination program; XS, the Bruker SHELXS module for the solution of X-ray crystal structures from diffraction data; XL, the Bruker SHELXL module for structure refinement; XP, the Bruker interactive graphics display module for crystal structure). The H atoms were included, their Uiso thermal parameters fixed at either 1.2 or 1.5 (depending upon their atomic environment) of the value of the Uiso of the atom to which they were attached and forced to ride that atom. The final standard residual R$_1$ value for diol acetonide 8 was 0.0661 for observed data and 0.0766 for all data. The corresponding Sheldrick R values were wR$_2$ of 0.1863 and 0.2048, respectively. The goodness-of-fit on F$^2$ was 1.065. The structure of one of the molecules of the diol acetonide 8, present in the unit cell is shown in FIG. 2. The Flack absolute structure parameter (See: Flack, H. D. Acta Cryst. 1983, 876881) was −0.4(3). A final difference Fourier map showed minimal residual electron density; the largest difference peak and hole being +0.585 and −0.398 e/Å3. Final bond distances and angles were all within expected and acceptable limits.

1-Isopancratistatin 1,2 Cyclic Sulfate-3,4-acetonide
(12)

To a solution of diol 8 (0.25 g, 0.67 mmol) in THF (10 ml)-triethylamine (0.4 ml, 2.9 mmol) was added thionyl chloride (0.1 ml, 1.37 mmol, 2 equiv.). The reaction was carried out at room temperature under argon for 40 minutes. Ethyl acetate (50 ml) was added and the organic layer was washed with water (2×10 ml) followed by brine (10 ml). After drying and concentrating, an off white solid (0.26 g, 93%) was obtained. The $^1$H NMR (CDCl$_3$, 300 MHz) indicated the sulfite product (12) was obtained as a mixture of epimers. The solid (0.26 g, 0.63 mmol) was dissolved in CH$_3$CN (15 ml)-CCl$_4$ (12 ml), RuC$_{13}$.H$_2$O (0.24 g, 0.115 mmol, 0.5 equiv.) and NaIO$_4$ (0.48 g, 2.24 mmol, 3 equiv.) were added together as a solid, followed by water (12 ml). The mixture was stirred at room temperature for 19 hours. Ethyl acetate (80 ml) was added and the organic layer separated, washed with water (2×15 ml) dried (MgSO$_4$), filtered through a pad of silica gel, and concentrated to a brown solid which was dried under high vacuum for 16 hours (0.13 g, 45%). Recrystallization from THF: hexane provided a white amorphous solid: R.f 0.7 (96:4 $CH_2Cl_2$—$CH_3OH$); $[\alpha]^{24}_D$=+7.3 (c 0.15, THF); m.p. 223° C.; $^1H$ NMR (DMSO 500 MHz) δ 13.1 (s, 1H) 9.06 (s, 1H), 6.39 (s, 1H), 6.11 (d, J=1 Hz, 1H), 6.09 (d, J-1 Hz, 1H), 5.58 (t, J=7.5 Hz, 1H), 5.26 (dd, J-7.0, 9.0 Hz, 1H), 4.71 (dd, J-7.8, 9.3 Hz, 1H), 4.6 (t, J-8 Hz, 1H), 3.74 (dd, J-7.8, 14.8 Hz, 1H), 3.66 (dd, J-8, 14 Hz, 1H), 1.47 (s, 3H), 1.35 (s, 3H); $^{13}C$ NMR (DMSO 500 MHz) 168.3, 152.5, 145.5, 133.0, 132.5, 110.8, 102.3, 97.5, 84.4, 82.5, 77.0, 73.2, 56.0, 50.2, 37.2, 27.1, 25.0. EIMS m/z (%): 427 (M+100), 412 (10), 396 (1.7), 370 (2.6), 352 (3.5), 327 (10.5), 272 (21), 242 (36), 218 (10.5), 205 (29), 147 (17), 119 (9.6), 85 (8.7), 60 (1.7), 44 (42). Anal. Calcd for $C_{17}H_{17}O_{16}NS$: Calcd C, 47.8; H, 4.01; N, 3.27; Found C, 48.08; H, 4.16; N, 3.13.

Pancratistatin 1-Benzoate (13)

To a solution of cyclic sulfate 12 (0.09 g, 0.21 mmol) in DMF (2 ml) was added benzoic acid (0.042 g, 0.36 mmol, 1.7 equiv.) followed by $Cs_2CO_3$ (0.1 g, 0.31 mmol, 1.5 equiv.). The mixture was stirred under argon at 60° C. for 4 hours. The DMF was removed (high vacuum) and the residue was suspended in THF (2 ml). Water (3 drops from a pipette) followed by $H_2SO_4$ (conc. 2 drops from a pipette) (See: Trost, B. M.; Pulley, S. R. *J. Am. Chem. Soc.*, 1995, 117, 10143–10144) was added and the suspension became a solution. The solution was stirred at 70° C. for 24 hours. Additional THF (2 ml), water (2 drops) and $H_2SO_4$ (2 drops) were added and the reaction was allowed to continue for 2 hours. The crude reaction mixture was separated by passing through a silica gel flash column (9:1 $CH_2Cl_2$—$CH_3OH$). The product was collected and recrystallized by dissolving in 9:1 $CH_2Cl_2$—$CH_3OH$, concentrating to a viscous oil, followed by solution in chloroform and addition of hexane to turbidity. The benzoate (13) recrystallized at room temperature, a colorless amorphous solid weighing 0.066 g, 74%; $[\alpha]^{24}_D$=-21° (c 0.19 $CH_3OH$); m.p. 180–185° C.; $^1H$ NMR (DMSO 500 MHz) δ 13.2 (s, 1H), 7.98 (m, 3H), 767 (t, J=9 Hz, 1H), 7.52 (t, J=10 Hz, 2H), 6.25 (s, 1H), 6.07 (d, J=1.5 Hz, 1H), 6.02 (d, J=1.5 Hz, 1H), 5.8 (bs, 1H), 5.68 (s, 1H), 4.96 (bs, 1H), 4.14–4.09 (m, 2H), 3.93–3.86 (m, 2H), 3.37 (m, 1H); $^{13}C$ NMR (DMSO 500 MHz) 169.3, 165.4, 152.1, 145.7, 134.0, 133.4, 132.2, 129.6, 129.5, 129.1, 128.6, 128.3, 107.3, 101.9, 95.7, 71.7, 70.0, 69.9, 68.8, 50.6, 38.0; EIMS m/z (%): 429 (M+, 12.5), 325 (3.5), 307 (9.8), 271 (15.2), 247 (50), 218 (9.8), 205 (7), 122 (69.6), 105 (100), 77 (80), 52 (46), 28 (53). Anal. Calcd for $C_{21}H_{19}O_9N.H_2O$: Calcd: C, 56.38; H, 4.73; N, 3.13; Found: C, 56.82; H, 4.61; N, 2.95.

(+)-Pancratistatin (1a)

A methanol (0.5 ml) solution of benzoate 13 (0.025 g, 0.058 mmol) was treated with $K_2CO_3$ for 16 hours at room temperature. TLC (5:1 $CH_2Cl_2$—$CH_3OH$) showed product development with starting material still present. The reaction mixture was heated to 55–60° C. for 3 hours whereby TLC showed no starting material present. The mixture was concentrated to a brown solid and the residue was dissolved using a mixture of DMF (0.4 ml) and 9:1 $CH_2Cl_2$—$CH_3OH$. The crude material was purified by passage through a column of silica gel with 4:1 $CH_2Cl_2$—$CH_3OH$ as the eluent, to afford (+)-pancratistatin (1a) as an off white solid (0.014 g, 75%); R.f. 0.38 (4:1 $CH_2Cl_2$—$CH_3OH$); m.p. with dec. 265–270° C.; $^1H$ NMR (DMSO 500 MHz): δ 13.05 (s, 1H), 7.49 (s, 1H), 6.48 (s, 1H), 6.05 (s, 1H), 6.02 (s, 1H), 5.36 (bs, 1H), 5.07 (m, 2H), 4.82 (d, J=7 Hz, 1H), 4.27 (s, 1H), 3.95 (1bs, 1H), 3.84 (bs, 1H), 3.72 (m, 2H), 2.96 (d, J=12.5 Hz, 1H); $^{13}C$-NMR (DMSO 500 MHz) d 169.5, 152.0, 145.4, 135.6, 131.7, 107.5, 101.7, 97.7, 73.3, 70.2, 69.9, 68.5, 50.5. Comparison (NMR, IR, TLC) with an authentic specimen of natural (+)-pancratistatin confirmed the mutual identity of the synthetic and natural samples.

From the foregoing, it is readily apparent that all of the aforestated objects have been realized by the invention described above. Such modifications, alterations and variations as may be apparent to an artisan having ordinary in the art to which this invention pertains are included within the spirit of the present invention which is limited solely by the scope of the claims appended hereto.

What is claimed is:

1. The method of synthesizing pancratistatin comprising epoxidating natural (+)-narciclasine to an epoxide, reducing said epoxide to a diol, converting said diol to a cyclic sulfate, creating a ring opening in said cyclic sulfate with cesium benzoate, and saponifying said benzoate to (+)-pancratistatin.

2. The method of synthesizing (+)-pancratistatin comprising preparing 3,4 narciclasine acetomide; protecting the C-2 and C-7 hydroxyls of said acetonide by acetylation to form a diacetate; oxidizing said diacetate with m-chloroperoxybenzoic acid in dichloromethane and a phosphate buffer to form an epoxide; hydrogenating said epoxide in the presence of 10% palladium on carbon and thereafter saponifying the hydrogenated epoxide to yield a mixture including trans B/C diol; isolating said trans B/C diol from said mixture and treating it with thinoyl chloride to form epimeric (sulfoxide)cyclic sulfites; oxidizing said cyclic sulfites to form the corresponding cyclic sulfate using ruthenium trichloride and sodium iodate in the presence of excess oxidant; hydrolyzing said cyclic sulfate in tetrahydrofuran using sulfuric acid to form a benzoate; and removing the benzoyl group from said benzoate to yield (+)-pancratistatin.

* * * * *

UNITED STATES PATENT AND TRADEMARK OFFICE
CERTIFICATE OF CORRECTION

| | | |
|---|---|---|
| PATENT NO. | : 6,949,647 B2 | |
| APPLICATION NO. | : 10/450917 | |
| DATED | : September 27, 2005 | |
| INVENTOR(S) | : George R. Pettit et al. | |

It is certified that error appears in the above-identified patent and that said Letters Patent is hereby corrected as shown below:

Column 1, line 10, "may have" should be changed to --has--.

Signed and Sealed this

Twelfth Day of May, 2009

JOHN DOLL
*Acting Director of the United States Patent and Trademark Office*